United States Patent [19]

Gyure et al.

[11] Patent Number: 5,103,005
[45] Date of Patent: Apr. 7, 1992

[54] METHOD FOR RECOVERY OF RIBOFLAVIN

[75] Inventors: Dale C. Gyure, Westminster; George W. Lauderdale, Greeley, both of Colo.

[73] Assignee: Coors Biotech, Inc., Westminster, Colo.

[21] Appl. No.: 383,876

[22] Filed: Jul. 21, 1989

[51] Int. Cl.$^5$ .............................. C07D 475/14
[52] U.S. Cl. .................................... 544/251
[58] Field of Search ........................ 544/251

[56] References Cited

U.S. PATENT DOCUMENTS

| | | | |
|---|---|---|---|
| 2,324,800 | 7/1943 | Pasternack et al. | 544/251 |
| 2,797,215 | 1/1957 | Dale | 544/251 |
| 2,815,341 | 12/1957 | Dale | 544/251 |
| 2,822,361 | 2/1958 | Morehouse | 544/251 |
| 4,567,262 | 1/1986 | Grimmer et al. | 544/251 |
| 4,687,847 | 8/1987 | Grimmer et al. | 544/251 |

FOREIGN PATENT DOCUMENTS

| | | |
|---|---|---|
| 0137226 | 4/1985 | European Pat. Off. . |
| 3247381 | 6/1984 | Fed. Rep. of Germany . |
| 3421714 | 12/1985 | Fed. Rep. of Germany . |
| 52-110897 | 11/1977 | Japan . |

OTHER PUBLICATIONS

Biotechnology vol. 4, pp. 127-132 (ed. Rehm & Reed 1986).
Economic Microbiology, vol. 2, p. 314 (ed. Rose 1978).
Hoffmann LaRoche "Rovimix B$_2$ 80 SD" data sheets.

*Primary Examiner*—C. Warren Ivy
*Assistant Examiner*—Celia Chang
*Attorney, Agent, or Firm*—Sheridan, Ross & McIntosh

[57] ABSTRACT

A method for the recovery of riboflavin from a fermentation broth or other feed stock is disclosed. The method comprises a process for the production of large, pure riboflavin crystals from an alkaline, aqueous solution containing solubilized riboflavin. The method can further comprise the process for production of large, pure riboflavin crystals in combination with two solids/liquid separation steps, the latter of which can result in a final riboflavin product purity of at least about 96% by weight.

35 Claims, 2 Drawing Sheets

FIG. 3

METHOD FOR RECOVERY OF RIBOFLAVIN

FIELD OF THE INVENTION

The instant invention relates to a process for the recovery of riboflavin from fermentation broths and other solutions containing more than 0.2 grams per liter (g/l) riboflavin and purification thereof to at least 96% by weight.

BACKGROUND OF THE INVENTION

Riboflavin, also known as vitamin $B_2$, vitamin G and lactoflavin, has physiological significance in the metabolism of protein, fat, and nucleic acids. Because it is considered to be an essential B vitamin, riboflavin is added to poultry and livestock feeds as well as human foodstuffs to supplement naturally occurring levels.

Riboflavin has typically been produced by chemical synthesis or by fermentation. Chemical synthesis can result in a riboflavin product contaminated with reactant or byproduct chemicals. Purification of riboflavin by removal of said contaminants can be expensive. Moreover, the synthetic process can result in the generation of toxic or hazardous wastes that must be properly disposed.

For these reasons, a "natural" riboflavin product can be preferred by manufacturers of human and animal food products. Because "natural" riboflavin is produced by the fermentation process, its impurities are largely cellular structures and moieties. Such impurities do not present the toxicity hazards or disposal problems that chemical reactant or byproduct contaminants can present.

However, riboflavin produced by recovery from fermentation broth has typically had an inferior level of purity compared to riboflavin produced by chemical synthesis.

A method for recovery of riboflavin from fermentation broth is described in U.S. Pat. No. 2,822,361 to Morehouse (1958). The Morehouse method involves the following steps: (1) heating of a fermentation broth having a pH of 4.5-5.0 to lyse the cells and dissolve the riboflavin; (2) filtering to separate cells from solubilized riboflavin; (3) precipitating the riboflavin in a reduced form by the treatment of the filtrate with a reducing agent; (4) adjusting the pH to at least 9.5 to solubilize the reduced riboflavin precipitate; (5) oxidizing the reduced riboflavin in the high pH solution; (6) precipitating the oxidized riboflavin from the high pH solution by adjustment of the pH to 4.0-7.5; and (7) separating the riboflavin precipitate from its mother liquor. The starting material for the Morehouse method is a fermentation broth containing about 1 g/l riboflavin. The purity of the final product is reported to be 87%.

Other patents involving riboflavin recovery or conversion of riboflavin from one crystal type to another appear to be cumulative of steps found in the Morehouse process. The precipitation of the "riboflavin precurser" and its subsequent oxidation in the method of U.S. Pat. No. 2,815,341 to Dale (1957) appears to be cumulative of the Morehouse steps of precipitation of the riboflavin in reduced form followed by oxidation. Additionally, the solubilization of riboflavin by adjustment of the pH to alkali conditions and the subsequent step of riboflavin crystallization by reducing the pH by acidification in U.S. Pat. No. 2,797,215 to Dale (1957) appears to be cumulative to the Morehouse steps of solubilization of riboflavin followed by crystallization.

The Morehouse method has the drawback that it cannot recover the majority of riboflavin from concentrated (i.e., more than 1 g/l) riboflavin starting solutions due to its method for solubilization of riboflavin, i.e., by heating the broth. Separation of riboflavin from the cells in the broth is accomplished by hot filtration. Because only relatively small amounts of riboflavin can be solubilized by heating, the Morehouse method is not suitable for starting solutions containing riboflavin in concentrations greater than about 1 g/l.

Consequently, there is a need for a method for recovery of riboflavin from fermentation broths and other materials having a riboflavin concentration greater than 1 g/l. Moreover, a method should preferably produce a final riboflavin product having a purity comparable to that of riboflavin produced by chemical synthesis. The method should be relatively simple so as to reduce the costs inherent in lengthy and complex procedures such as Morehouse It has been found that the present invention can satisfy the above requirements. The instant process has additional advantages over known recovery procedures. The subject method contains only one riboflavin precipitation step and therefore shortens process time and lessens expense compared to the Morehouse process. Further, the precipitation of oxidized or non-reduced riboflavin in the instant process can be accomplished directly from a fermentation broth rather than from a purified riboflavin solution as provided by Morehouse and Dale (U.S. Pat. No. 2,797,215). The present method also produces a product having a purity comparable to the purity of chemically synthesized riboflavin.

SUMMARY OF THE INVENTION

The present invention involves a method for controlling the size and purity of riboflavin crystals during the crystallization process. It has been found that the riboflavin crystals produced by the crystallization process of reducing the pH of an aqueous, alkaline solution containing solubilized riboflavin, increase in size and purity as the concentration of oxidant increases. In one embodiment, the method of the present invention involves contacting an aqueous, basic solution containing solubilized riboflavin with an oxidant while reducing the pH of said solution to between about 3.0 and about 10.0 to produce large, pure riboflavin crystals.

In a second embodiment the process of riboflavin crystallization in the presence of an oxidant is carried out in combination with two solid/liquid separation procedures. An aqueous solution containing solubilized riboflavin and having a pH of at least about 10.0 undergoes a first solid/liquid separation process to separate the solubilized riboflavin from contaminants larger in size than the solubilized riboflavin to produce a partially-purified riboflavin solution. The partially-purified riboflavin solution is then contacted with an oxidant while its pH is reduced, resulting in a slurry containing large, pure riboflavin crystals. The riboflavin crystals are then separated from the contaminants in the slurry smaller than the crystals to produce a riboflavin product of high purity.

In another embodiment, the feed stock to the present method is a fermentation whole broth containing extracellular riboflavin in a concentration of at least 0.2 g/l and up to 10 g/l or greater. The feed stock can be stored and/or concentrated prior to solubilizing the riboflavin therein. The riboflavin is solubilized by adjusting the pH of the whole broth to between about 11.5 and about 13.5. The high pH whole broth solution then undergoes a solids/liquid separation process to separate the solubilized riboflavin from cells and cellular moieties larger in size than the riboflavin. The partially-purified high pH broth containing solubilized riboflavin is then contacted with an oxidant while its pH is adjusted to between about 3.0 and about 10.0, resulting in a slurry containing large, pure riboflavin crystals. The crystal slurry can next be stored and/or concentrated. The riboflavin crystals are then separated from the contaminants in the slurry smaller than the riboflavin crystals to produce a riboflavin product of high purity. The riboflavin crystals can then be dried to produce a final product having a purity of at least about 96% by weight.

DETAILED DESCRIPTION OF THE INVENTION

The instant invention involves a process for the formation of high purity riboflavin crystals. The process allows substantial control of the crystal size and permits the formation of large crystals which can be more readily separated from contaminants. The instant process comprises precipitating the riboflavin from an alkaline aqueous solution containing riboflavin in a concentration of at least 0.2 g/l and up to 10 g/l or more in the presence of an oxidant. In another embodiment, the instant process involves the precipitation process in combination with at least two liquid/solid separation steps to provide a high purity riboflavin product.

In the instant method for precipitating riboflavin crystals, an aqueous, basic solution containing solubilized riboflavin is contacted with an oxidant while the pH of the solution is reduced by the addition of an acid. It has been found that unexpectedly the size and size distribution of the riboflavin crystals and the purity of the crystals are determined by the concentration of oxidant in the riboflavin-containing solution during pH adjustment. It has also been found that the final purity of the riboflavin product is affected by the concentration of oxidant in the riboflavin-containing solution during pH adjustment. The riboflavin which crystallizes and precipitates in the presence of the oxidant has been found to be more heat stable during subsequent crystal drying processes than riboflavin precipitated in a reducing environment. This improved relative heat stability of riboflavin crystallized in the presence of an oxidant results in less degradation of riboflavin into contaminants during subsequent drying steps, providing greater purity in the final riboflavin product.

Riboflavin is commonly solubilized by increasing the pH of an aqueous mixture containing riboflavin to above about 10.0. In the instant process oxidized or non-reduced riboflavin is crystallized from the aqueous, alkaline solution by contacting the solution with an oxidant while lowering the pH by the addition of an acid to a pH between about 3.0 and about 10.0. Preferably the pH is adjusted to between about 5.8 and about 6.2. The high pH solution should contain a concentration of oxidant sufficient to at least minimize the likelihood of formation of reduced riboflavin crystals during acidification. The oxidant is any composition that either oxidizes riboflavin to its oxidized state or prevents the formation of reduced riboflavin in the alkaline solution and/or during acidification. The oxidant used in the instant process should be readily separable from riboflavin to prevent contamination of the final riboflavin product. The oxidant can be air, pure oxygen, purified air, hydrogen peroxide, permanganate, nitrates, sulfites, sodium bismuthate, ammonium peroxodisulfate, sodium peroxide, potassium bromate, potassium dichromate, potassium iodate or ozone.

As discussed hereinabove, it has been found that the oxidant concentration during riboflavin precipitation is critical. It has been found that larger, purer riboflavin crystals are produced by the crystallization of riboflavin in a non-reduced or oxidized state. These are obtained if sufficient oxidant is present. As discussed hereinabove, it has been found that if riboflavin is crystallized in a non-reduced or oxidized form, it has greater thermal stability in subsequent drying steps relative to riboflavin crystallized in reduced form. Because riboflavin crystallized in a reducing environment is less heat stable during downstream drying processes, it can degrade into a variety of byproducts and decrease the final product purity. The structures of riboflavin in its reduced and oxidized states, and configurations of oxidized riboflavin at different pH's are illustrated below:

-continued
Oxidized (insoluble)

If the oxidant used is air, oxygen or purified air, the alkaline solution is placed in a tank containing means for introducing gas such as a sparge ring. The high pH solution normally has essentially 0% dissolved oxygen before aeration; therefore, aeration is preferably initiated prior to decreasing the pH in order to provide a sufficient concentration of oxidant. Aeration is continued until the oxygen concentration is preferably 50% to 100% of saturation. With vigorous aeration, nearly 100% dissolved oxygen can be achieved in a relatively brief time so as to enhance the likelihood of formation of non-reduced crystals. Under preferred operating conditions, aeration is vigorous enough to maintain dissolved oxygen near 100% of saturation.

The oxygen demand for a high pH solution containing about 10 g/l riboflavin has been determined by a dissolved oxygen meter to be at least about 5 ppm (w/v). The oxygen demand is defined as that quantity of dissolved oxygen necessary for substantially all of the riboflavin crystals to form in an oxidized or non-reduced state during acidification. The preferred quantity of oxygen or oxidizing agent is therefore estimated as between about 5 ppm and about 500 ppm, depending on the strength of the oxidant. For example, if aeration is used, it should be continued until at least about 5 ppm of oxygen is present in the high pH solution. Because the solubility of oxygen in an alkaline solution at 20° C. is about 7 ppm (based on weight per volume, hereinafter "w/v"), the aeration of the high pH solution to between about 50% and about 100% of saturation provides the necessary oxidizing environment. It has been found that as the oxygen concentration drops below about 50% of saturation, the riboflavin can crystallize in reduced form resulting in a lower riboflavin product purity, and crystal size can diminish. Consequently these conditions can result in a final riboflavin product having a purity of less than 96% by weight Under preferred precipitation conditions, the raw crystal slurry has an orange color. 100% oxygen saturation of the permeate has been found to produce needle crystals that are about 20 to about 100 microns in length or longer with an aspect ratio greater than about 50. The precipitate contains needles that are randomly oriented rather than aligned in a "haystack" configuration. There are few, if any, fines, i.e., needles having a length of less than 2 microns.

Once an oxidant is present in the high pH solution in a appropriate concentration, the pH can be slowly adjusted to between about pH 3.0 and about 10.0, preferably to between about 4.5 and about 8.0, and most preferably to between about 5.8 and about 6.2. As pH is lowered, the riboflavin crystallizes and precipitates to form a crystal slurry. Any acid that can reduce the pH to between about 3.0 and about 10.0 and can be readily separated from the solid riboflavin, can be used including without limitation sulfuric acid, hydrochloric acid, hydrofluoric acid, acetic acid and trichloroacetic acid. The acid should be added in a manner to minimize local pH gradients. Mechanical mixers can be used to mix the acid quickly. Foaming can occur as the pH is decreased in the range of about pH 8 to 7, but such foaming normally subsides below about pH 6.5. Foaming is a function of protein solubility at variable pH's and has no effect on the precipitation of riboflavin.

The temperature of the solution during aeration and pH reduction is preferably maintained between about 60° and about 100° F., more preferably between about 75° and about 85° F. Because the pH adjustment is exothermic, the adjustment should either be gradual to allow for dissipation of heat or means of cooling should be provided in the oxidation/pH reduction vessel. If temperature exceeds 100° F., riboflavin solubility and degradation increases. This can result in decreased riboflavin recovery and purity.

If the riboflavin precipitation step of the present method is carried out on a continuous rather than batch basis, a "heel" or residual fraction of raw crystal slurry can remain in the oxidation/pH reduction vessel to facilitate precipitation. Because raw crystal slurry can support bacterial growth, a raw crystal slurry heel can cause ongoing bacterial contamination in newly produced raw crystal slurry. Therefore, the utility of the slurry heel in facilitating crystallization must be weighed against the risk of bacterial contamination.

Figure 1:
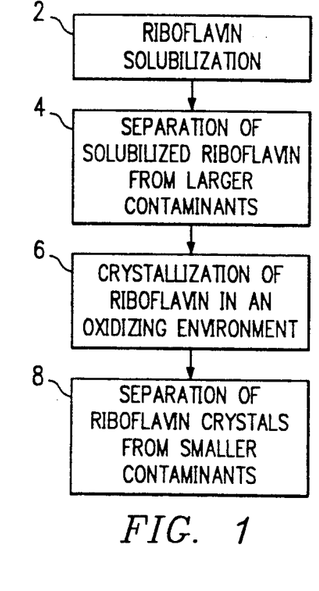
FIG. 1 is a schematic flow chart of the method of precipitating riboflavin crystals in combination with two solids/liquid separation steps.

The method for precipitating riboflavin crystals can also be carried out in combination with two liquid/solid separation steps. This embodiment comprises the following steps: solubilizing riboflavin in a fermentation broth or other starting material by adjusting the pH of the broth to between about 11.5 and about 13.5; separating the solubilized riboflavin from larger components in solution including whole cells and cellular debris; crystallizing the riboflavin by lowering the pH of the riboflavin-containing solution while contacting the solution with an oxidant; and separating the riboflavin crystals from smaller fermentation contaminants in the acidified solution. These process steps are depicted in the flowchart of FIG. 1. The process steps can be carried out on a batch or continuous basis.

A feed stock of, for example, fermentation whole broth containing extracellular crystalline riboflavin is treated with a base to raise the pH and solubilize riboflavin. Solubilization of the riboflavin permits the separation of riboflavin from whole cells, cellular debris and cellular moieties greater in size than solubilized riboflavin. To solubilize the riboflavin, the pH of the whole broth is preferably adjusted to a pH in the range of about 11.5 and about 13.5, more preferably to a pH of about 12.0 to about 13.0, and most preferably to a pH of about 12.4 to about 12.8. The pH adjustment is preferably accomplished in a manner to minimize local pH gradients. This can be accomplished by agitation using a mechanical mixer. The alkali metal hydroxides, including sodium hydroxide, potassium hydroxide and lithium hydroxide, or any base capable of achieving the desired pH range, can be used for pH adjustment in the present method.

The temperature of the solution during riboflavin solubilization should be maintained between 60° and 100° F., preferably between 75° and 85° F. Above about 100° F., riboflavin begins to degrade particularly at alkaline pH's. If the temperature drops below about 60° F., riboflavin begins to crystallize, even though the pH is above 11.5.

In the most preferred pH range of 12.4 to 12.8, the riboflavin solubility is greater than 50 g/l. However, even in the most preferred pH range, riboflavin does not remain in solution indefinitely and can begin to crystallize within hours. This loss in solubility may be due to the change in whole broth composition resulting from whole cell leaching at elevated pH values. Riboflavin crystallization due to whole cell leaching can be slowed by heating the solution; however, heating the solution can also accelerate the degradation of riboflavin. To minimize the loss of riboflavin, it is preferred that the separation of the solubilized riboflavin from the cells, cellular debris and macromolecules, be completed expeditiously following solubilization of the riboflavin.

Referring now to FIG. 1, the first solid/liquid separation stage separates a substantial portion of the contaminants larger than solubilized riboflavin from the solubilized riboflavin in the alkaline fermentation broth. The phrase "separates a substantial portion of the contaminants" as used herein means a separation of at least about 75% by weight of the components larger than solubilized riboflavin from the solubilized riboflavin. Any of the solid/liquid separation methods known in the art can be used, including, in increasing preference, gravimetric settling, centrifugation, vacuum or pressure filtration, or ultrafiltration. A combination of separation methods can also be used. The temperature of the permeate, filtrate or supernatant should be maintained between about 60° and 100° F., preferably between about 75° and 85° F., to minimize riboflavin degradation or crystallization. It is preferred that this step be accomplished by dialysis on the ultrafilter because a more effective separation of solubilized riboflavin from cells, cellular debris, larger soluble cellular moieties and insoluble cellular moieties can be obtained. This provides not only a greater yield, but also a higher riboflavin final product purity. The separation of solubilized riboflavin from cells, debris and macromolecules at this stage is critical in the preferred scheme of the instant process because there is no later step for the separation of riboflavin from larger contaminants such as whole cells or cellular structures or moieties.

As discussed in detail hereinabove, crystallization 6 of non-reduced riboflavin from the high pH permeate is accomplished by contacting the alkaline permeate with an oxidant while lowering the pH from between about 11.5 and about 13.5 to between about 3.0 and about 10.0. The crystallization process results in a raw crystal slurry.

The second solids/liquid separation stage 8 involves the separation of riboflavin crystals, having a length of about 20 to about 100 microns or longer, from soluble and smaller suspended fermentation impurities in the crystal slurry. The separation of a substantial portion of the contaminants smaller than the riboflavin crystals from the crystals is accomplished by crystal washing or dialysis. Crystal "washing" or "dialysis" means the use of a liquid stream to carry away impurities. The terms "washing" and "dialysis" are used interchangeably herein. Crystal washing can be accomplished by several liquid/solid separation methods known in the art including, in order of increasing preference, gravimetric settling, centrifugation, vacuum or pressure filtration, or ultrafiltration. A combination of said separation methods can also be used. In one preferred embodiment, ultrafiltration provides an effective separation of crystallized riboflavin from the smaller soluble and suspended cellular moieties (e.g., proteins) contained in the crystal slurry, thereby resulting not only in a greater yield, but also in a higher riboflavin purity. In another preferred embodiment, effective separation of crystallized riboflavin from smaller soluble and suspended cellular moieties is accomplished by rotary vacuum filtration. The separation of crystallized riboflavin from soluble and suspended cellular moieties at this stage is critical because removal of smaller cellular moieties from the riboflavin crystals improves the final product purity.

Figure 2:
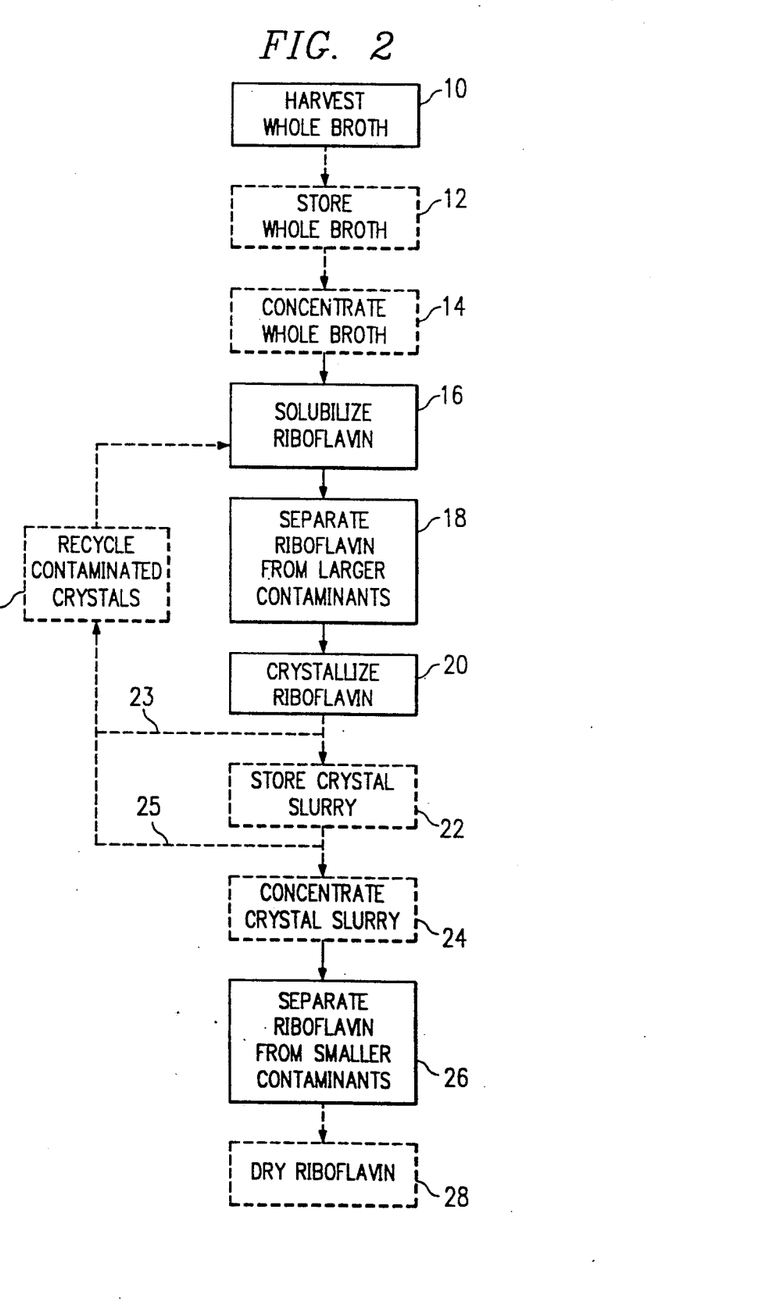
FIG. 2 is a schematic flow chart of a preferred method of recovering riboflavin.

In a preferred embodiment of the present process depicted in FIG. 2, the method of the present invention is carried out using ultrafiltration in the two solid/liquid separation steps. Referring now to FIG. 2, a preferred feed stock for the present method, whole broth, is harvested 10 from a fermenter. Microorganisms preferred for providing the whole broth are those which are capable of synthesizing riboflavin and transporting the same extracellularly. *Candida flareri* is one such microorganism. However, any yeast, bacteria, mold or plant tissue culture capable of synthesizing and transporting riboflavin extracellularly can be used. It is also contemplated that a fermentation broth in riboflavin is produced and retained intracellularly and in which the cells have been lysed to release riboflavin can be used as a feed for the instant process. If a lysing procedure is used, the means of cell lysing cannot degrade a large proportion of the riboflavin.

The present method can also be used to recover and purify riboflavin from other feed stocks. A riboflavin product of 50% purity produced by recovery of riboflavin from a fermentation broth can be used as feed stock in the instant process. As is discussed hereinafter, an off-specification (less than 96% pure) riboflavin product of the instant process whose poor purity resulted from, for example, apparatus failure, can be used as a feed stock. Additionally, a synthesized riboflavin product containing chemical byproduct contaminants can also be used as a feed stock. The present method can be used in any situation where the formation of large, pure riboflavin crystals during the precipitation of riboflavin is important.

In order for riboflavin to be recovered by the present method, the feed stock must have an extracellular riboflavin concentration greater than the riboflavin concentration at which saturation occurs for the temperature and pH conditions used in the present method. Saturation means the solute concentration beyond which further addition of solute to the solution results in no further dissolution of the solute but rather the precipitation of the solute. Because the present method recovers riboflavin in crystalline form, the riboflavin in the feed stock must be in excess of saturation before any recovery can be expected. Riboflavin saturation in an aqueous environment having a pH of between about 5.0 and about 6.0 and a temperature of about 70° F. occurs at a concentration of about 0.2 g/l. This means that if the riboflavin concentration in the feed stock is less than 0.2 g/l under the stated pH and temperature conditions, there will be no riboflavin recovery by the instant process. The greater the concentration of riboflavin in the whole broth or other feed stock, the greater the overall riboflavin yield can be.

The whole broth is harvested 10 from the fermenter. The pH of the broth is typically about 5.0. The whole broth can immediately undergo the step of riboflavin solubilization 16, or the broth can be stored 12. Any storage of the whole broth should preferably be conducted under conditions of moderate aeration to facilitate $CO_2$ degassing and at a temperature of between about 59° and 86° F. Reasonable measures should be taken to prevent contamination by foreign microorganisms which can decrease yield. However, the method of the present invention has been found to be successful with severely contaminated whole broth. "Severely contaminated" as used herein means a broth having a weight ratio of contaminating microorganisms to resident microorganisms of about 1:1 or greater. Storage does allow for the metabolism by the yeast or other resident microorganism of nutrient contaminants, which in turn reduces the opportunity for contamination by foreign microorganisms. However, storage is not necessary for the successful operation of the present invention.

Also prior to the step of riboflavin solubilization 16, the fermentation whole broth can be concentrated 14 by the removal of water and small water-solubles to provide: (1) preferably at least about a 75% reduction in volume of the broth; (2) a riboflavin concentration in the broth of at least about 20 g/l; or (3) a total suspended solids concentration of at least about 180 g/l. Concentration of whole broth can be accomplished by any means known in the art suitable for separating cells and extracellular crystallized riboflavin from water and water solubles and suspended solids that are smaller than the extracellular crystallized riboflavin. Although any method suitable for such separation can be used, the following methods are preferred, listed in order of increasing preference: gravimetric settling, centrifugation, pressure or vacuum filtration, and ultrafiltration. A combination of said solid/liquid separation methods can also be used. The method of solids/liquid separation for purposes of concentration affects the final yield of riboflavin. In the case of gravimetric settling, the loss of riboflavin to the supernatant is likely to be great and riboflavin yield can decrease. With ultrafiltration, the cells and crystallized riboflavin are more effectively separated from water, and small solubles and suspended solids therein, resulting in a higher yield of riboflavin. However, the choice of solid/liquid separation for purposes of concentration has no effect on final purity of the riboflavin product.

If concentration of the whole broth is accomplished by ultrafiltration, a stirred cell or cup or a tangential flow or cross-flow ultrafilter can be used. The tangential flow ultrafilter has larger capacity and is therefore preferred for industrial scale use. The ultrafilter can be operated on a batch or continuous basis. A tangential flow ultrafilter such as the Koch-Abcor Corp.'s Ultrafiltration Unit with spiral wound membrane cartridges can be used. Concentration can be accomplished, for example, by setting the inlet pressure at between about 68 and about 72 pounds per square inch gauge (psig), resulting in an outlet pressure of between about 16 and 24 psig, and the recirculation rate, for example, at about 360 gallons per minute (gpm). The filter pore size used can be 1,000 to $1 \times 10^6$ MWCO or between about 0.0001 to about 0.1 micron. The filter used can include any filter whose composition can resist the pH conditions, temperature and pressures of the concentration step of the instant method without resulting in a rate of failure that makes the instant process economically infeasible. Useful membranes include the following: polysulfone membranes, ceramic membranes (e.g., zirconium oxide) and composite membranes (e.g., carbon on carbon). The ultrafilter retentate contains whole cells and crystallized riboflavin; the permeate is usually discharged. The temperature of the retentate during the concentration of the whole broth in the ultrafilter is preferably maintained between about 60° and about 100° F., more preferably between about 75° and about 85° F. If retentate temperature exceeds 100° F., degradation of membranes can occur in some cases. A minimum temperature of about 60° F. is preferred because the flux rate (rate of flow across the membrane) decreases as temperature decreases which increases process time.

The riboflavin is then solubilized 16 to permit the separation of riboflavin from the whole cells, cellular debris and macromolecules. The pH of the whole broth is adjusted to a pH preferably in the range of about 11.5 to about 13.5, more preferably to a pH of about 12.0 to about 13.0, and most preferably to a pH of about 12.4 to about 12.8. The solubilization step can be carried out, e.g., in a glass, fiberglass, plastic or metal vessel. As described hereinabove, the pH adjustment is preferably accomplished in a manner to minimize local pH gradients. This can be accomplished by agitation using a mechanical mixer. The temperature of the solution during riboflavin solubilization should be maintained between about 60° and about 100° F., preferably between about 75° and about 85° F. Above 100° F., riboflavin degrades at a faster rate, particularly at alkaline pH's. If the temperature drops below 60° F., riboflavin begins to crystallize, even though the pH is above 11.5.

If the whole broth has been concentrated in a crossfilter ultrafilter prior to the solubilization step, pH adjustment for purposes of riboflavin solubilization can be carried out in the ultrafilter itself. Solubilization can be accomplished by adding, for example, an aqueous solution having 50% by weight NaOH to the retentate while the ultrafilter is set on total recycle mode so that all permeate is returned to the retentate. The pH should not be measured until a sufficient amount of time has passed to assure complete mixing of the base. Verification that the filter is intact and that no cells or debris are passing into the permeate stream can be accomplished by checking the permeate microscopically. As described hereinabove, the temperature of the solution during riboflavin solubilization should be maintained between about 60° and about 100° F., preferably between about 75° and about 85° F. to avoid riboflavin degradation or crystallization. In the ultrafilter, temperatures above 100° F. at high pH's can result in a shorter filter life as well. Also, as solution temperature drops, the flux rate in the ultrafilter also decreases.

The separation 18 of solubilized riboflavin from cells, debris and larger cellular moieties in the high pH broth is preferably accomplished by dialysis in the ultrafilter. Separation by ultrafiltration is preferred to other solid/liquid separation steps because the effectiveness of separation goes directly to final product purity. During this step, the solubilized riboflavin and other high pH soluble moieties are washed into the ultrafilter permeate, while the whole cells, debris and larger cellular moieties remain in the retentate. Dialysis is conducted preferably with at least 10 volumes of soft water, i.e., water having a dissolved solids concentration of less than 0.3 g/l. The lower the solids concentration in the water used for dialysis, the greater the purity possible for the final riboflavin product.

The dialysis step can be carried out on a batch or continuous basis. When a cross-filter ultrafilter is used, the inlet and outlet pressures and recirculation rate can be set at those parameters set forth in the whole broth concentration step described hereinabove. Likewise, the filter compositions and filter pore sizes can be those specified in the discussion of whole broth concentration. Because of the significance of the crystal dialysis step to final riboflavin purity, an ultrafilter membrane failure at this stage results in a final riboflavin product having less than 96% purity. Verification that the filter is intact and that no cells or debris are passing into the permeate stream can be accomplished by checking the permeate microscopically.

The temperature of the retentate and permeate should be maintained at between about 60° and about 100° F., preferably between about 75° and about 85° F. to maximize filter life, minimize riboflavin degradation or crystallization, and maintain the flux rate at an acceptable level. The high pH is maintained in the retentate during dialysis by the continuous addition of an aqueous base such as 50% by weight NaOH. Dialysis is conducted until the riboflavin concentration in the retentate is less than some preselected level determined by acceptable yield losses. It is important that the riboflavin in the permeate remain solubilized until the time of contact of the permeate with an oxidant so that substantially all riboflavin can be crystallized in an oxidized or non-reduced state. To allow crystallization of riboflavin prior to contacting the high pH permeate with an oxidant can result in crystallization of the riboflavin in the reduced state which in turn can have a detrimental impact on final product purity, as discussed hereinabove.

Following separation of solubilized riboflavin from larger cellular components, the riboflavin is crystallized 20 in the presence of an oxidant. As discussed in detail hereinabove, crystallization of non-reduced riboflavin from the high pH permeate is accomplished by contacting the high pH permeate with an oxidant while lowering the pH from between about 12.4 and about 12.8 to between about 5.8 and about 6.2. This process is typically carried out in an aeration/precipitation vessel, rather than in the ultrafilter.

Following riboflavin crystallization and precipitation, the resulting crystal slurry should have no whole cell or cellular debris. If whole cell contamination is present, the contaminated crystal slurry 23 can be recycled 21 in the instant process to the riboflavin solubilization step 16, followed by separation 18 of solubilized riboflavin from cells and cellular debris, and crystallization 20 under oxidizing conditions.

Following riboflavin precipitation, the raw crystal slurry can immediately undergo crystal washing 26 or can be stored 22 prior to crystal washing. During storage, crystal size distribution can approach an equilibrium size and size distribution. There is no limit on the length of storage of the crystal slurry prior to crystal washing or dialysis. However, precautions should be taken to avoid bacterial contamination. Because raw crystal slurry can support microbial growth, it should be maintained at less than 77° F., and preferably below 59° F. Visible contamination of any sort present in the raw crystal slurry can result in the final material having a purity less than 96% because downstream steps of the present method are not directed to the removal of particulate contamination larger in size than the riboflavin crystals. If microscopic examination reveals microbial contamination in the raw crystal slurry, the contaminated slurry 25 can be recycled 21 in the instant process to the riboflavin solubilization step 16, followed by separation 18 of solubilized riboflavin from cells and cellular debris, and then crystallization 20 under oxidizing conditions.

Following the riboflavin crystallization and precipitation step 20, the slurry can also be concentrated 24 prior to crystal washing 26. Concentration can reduce the total volume of washing solvent needed for dialysis. The slurry is typically concentrated to a riboflavin concentration of between about 40 and about 70 g/l. The temperature of the crystal concentrate is preferably maintained in the range of about 60° to about 140° F., more preferably within the range of about 70° to about 110° F. Above 140° F., the riboflavin is more likely to degrade. Concentration can be accomplished by several known solid/liquid separation methods. Those methods, in order of increasing preference, include gravimetric settling, centrifugation, pressure or vacuum filtration (including rotary vacuum filtration), or ultrafiltration. A combination of said separation methods can also be used. As with the whole broth concentration step, the method of solid/liquid separation used for crystal slurry concentration is not critical. Less effective solid/liquid separation methods only decrease riboflavin yield and not final product purity.

If ultrafiltration is used to concentrate the crystal slurry, the filter pore sizes can be $1 \times 10^4$ MWCO to 5 microns. Filter compositions found to be useful for the crystal slurry concentration step are those identified hereinabove in the discussion of whole broth concentration. The ultrafilter inlet and outlet pressures and circulation rate can be set as described in the discussion of whole broth concentration. As discussed hereinabove, the retentate temperature is most preferably within the range of about 70° to about 110° F.

Alternately, if rotary vacuum filtration is used to concentrate the crystal slurry, a filter pore size of between about 5.0 and about 20.0 microns can be used.

Following riboflavin crystallization, the separation 26 of the riboflavin crystals from smaller contaminants in the concentrated slurry is preferably accomplished by crystal dialysis in the ultrafilter or by rotary vacuum filtration. Ultrafiltration and rotary vacuum filtration are preferred methods for separation of riboflavin crystals from smaller contaminants because of their effectiveness and because the dialysis step goes directly to final product purity. If, for example, the polysufone ultrafilter is used for crystal dialysis, the recirculation rate and inlet and outlet pressures can be set as specified hereinabove in the whole broth concentration step. Retentate temperature is preferably maintained between about 60° and about 140° F., more preferably between about 70° and 110° F. Filter pore size can be $1 \times 10^4$ MWCO to 5 microns. Filters found suitable for the crystal dialysis step include those identified hereinabove in the discussion of whole broth concentration.

Alternately, if rotary vacuum filtration is used to separate riboflavin crystals from smaller contaminants, a filter pore size of between about 5 and about 20 microns can be used.

The solvent used for crystal dialysis depends on the feed stock used in the instant process. If the feed stock is synthesized riboflavin containing organic chemical byproducts, volatile organic solvents, such as methanol, ethanol, pyridine, or hexane, can be used as the washing solvent to remove chemical byproducts. If the starting material is a whole broth or riboflavin-containing biomass, water is preferably used as the washing solvent.

If the solvent used is water, the crystal slurry is dialyzed with at least about 10 volumes of soft water, preferably having less than 0.3 g/l dissolved solids. Of course, if the crystal washing water has a lower solids concentration, the purity of the final riboflavin product is greater.

There are two alternate methods of washing riboflavin crystals with water. In the first method, the crystal slurry of roughly neutral pH is dialyzed or washed with 10 volumes of water having a pH of about 6.0. In the second method, the pH of the crystal slurry is adjusted to between about 9.6 and about 10.0 prior to washing or dialysis. Because water having a pH of about 6.0 is used to wash the crystals, the pH of the slurry decreases with washing from between about 9.6 and 10.0 to between about 6.8 and 7.2 with 10 volumes of wash. As it passes through the retentate, each volume of wash is at a different pH. This pH gradient allows components less soluble at near-neutral pH's to more easily pass across the ultrafilter membrane at higher pH's. The result is a higher final product purity.

After dialysis is complete, the concentrated washed crystal slurry is dried 28. Drying of the washed crystal slurry can be accomplished by any one of several methods known in the art including spray drying and flash drying to produce a riboflavin powder. If spray drying is used, the spray dryer inlet temperature is typically between about 419° and about 437° F. and the outlet temperature is typically between about 212° and 230° F.

If the crystal slurry was washed on a rotary vacuum filter drum, the resulting cake containing about 65% water can be dried by tray drying, oven drying, freeze drying, vacuum oven drying or infrared drying to produce a dry cake. The dry cake can then be ground with a mechanical grinding instrument to produce a riboflavin powder.

It has been observed that for off-specification products of the subject method, i.e., products that do not meet the 96% standard, recycling of the material to bring it to 96% purity requires that the material pass through all of the process steps beginning with solubilization 16 of the riboflavin at high pH, followed separation 18 of the solubilized riboflavin from larger cellular components, riboflavin crystallization 20 by adjusting the pH to about 6.0 in the presence of an oxidant, and separation 26 of riboflavin crystals from smaller contaminants in the crystal slurry. Repetition of the step of separation 26 of riboflavin crystals from smaller contaminants is usually not sufficient to raise the purity of the product to 96%.

Figure 3:
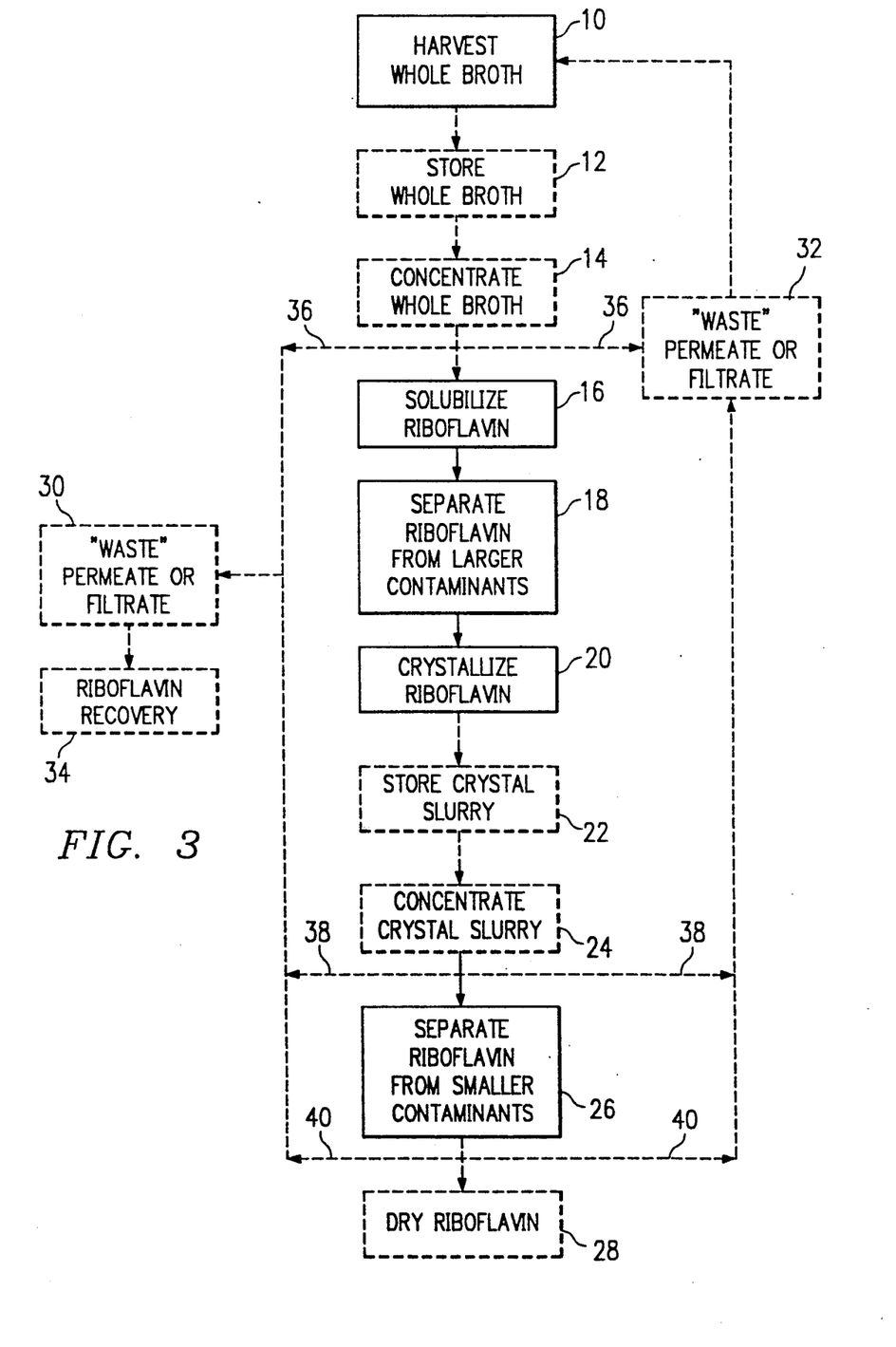
FIG. 3 is a schematic flow chart depicting alternate riboflavin recovery methods.

Referring to FIG. 3, riboflavin recovery from three waste streams of the instant process is illustrated. As discussed hereinabove, riboflavin is soluble at a pH of between about 5.0 and about 6.0 and at a temperature of about 70° F. only to about 0.2 g/l. The process illustrated in FIG. 2 is designed to recovery only crystalline riboflavin, i.e., riboflavin that is in excess of 0.2 g/l. Soluble riboflavin is lost in the discarded permeates, supernatants or filtrates produced by three different process steps: the concentration of whole broth 14 produces waste stream 36; the concentration of crystal slurry 24 produces waste stream 38; and the separation of riboflavin crystals from smaller contaminants 26 produces waste stream 40. Waste streams 36, 38 and 40 each comprise soluble riboflavin, small (e.g., 1 micron) riboflavin crystals and small, soluble and suspended cellular moieties such as proteins. These waste streams can be recycled 32 to the whole broth 10, but such recycling can expand the volume of feed stock. Instead, these waste streams 32 can an undergo an alternate recovery process 34, e.g., recovery by passing the waste permeate, filtrate or supernatant across a resin bed having an affinity for riboflavin until the bed is saturated, whereupon the riboflavin is eluted by a liquid that reduces the affinity of the resin for riboflavin.

While various embodiments of the present invention have been described in detail, it is apparent that modifications and adaptations will occur to those skilled in the art. However, it is to be expressly understood that such modifications and adaptations are within the spirit and scope of the present invention, as set forth in the following claims.

What is claimed is:

1. A method for the recovery of riboflavin from a first mixture comprising riboflavin and contaminants, said method comprising:
   (a) solubilizing the riboflavin in said first mixture by adjusting the pH of said first mixture to above about 10.0 to produce a second mixture;
   (b) separating contaminants that are larger than said solubilized riboflavin from said solubilized riboflavin in said second mixture to produce a third mixture comprising solubilized riboflavin and remaining contaminants;
   (c) precipitating riboflavin from said third mixture, wherein said third mixture is at a temperature of between about 60° F. and about 100° F., by reducing the pH of said third mixture and contacting said third mixture with an oxidant to produce a fourth mixture comprising riboflavin crystals and remaining contaminants; and
   (d) separating said riboflavin crystals from contaminants that are smaller than said crystallized riboflavin in said fourth mixture.

2. The method of claim 1, wherein said step of solubilizing the riboflavin while adjusting the pH comprises adjusting the pH to between about 11.5 and about 13.5.

3. The method of claim 1, wherein said step of solubilizing the riboflavin while adjusting the pH comprises adjusting the pH to between about 12.0 and about 13.0.

4. The method of claim 1, wherein said step of solubilizing the riboflavin while adjusting the pH comprises adjusting the pH to between about 12.4 and about 12.8.

5. The method of claim 1, wherein said step of reducing the pH of said third mixture comprises reducing the pH to between about 3.0 and about 10.0.

6. The method of claim 5, wherein said step of reducing the pH comprises reducing the pH to between about 4.5 and about 8.0.

7. The method of claim 6, wherein said step of reducing the pH comprises reducing the pH to between about 5.8 and about 6.2.

8. The method of claim 1, further comprising the step of concentrating said first mixture to obtain about a 75% reduction in volume of said first mixture, a riboflavin concentration of at least about 20 g/l, or a solids concentration of at least about 180 g/l, prior to said step of solubilizing said riboflavin.

9. The method of claim 1, further comprising the step of storing said first mixture prior to said step of solubilizing said riboflavin.

10. The method of claim 1, further comprising the step of storing said fourth mixture prior to said step of separating said riboflavin crystals from said remaining contaminants that are smaller than said crystallized riboflavin in said fourth mixture.

11. The method of claim 1, further comprising the step of concentrating said riboflavin crystals in said fourth mixture prior to said step of separating said riboflavin crystals from contaminants that are smaller than said crystallized riboflavin in said fourth mixture.

12. The method of claim 1, further comprising the step of drying said riboflavin crystal product.

13. The method of claim 1, wherein said first mixture comprises fermentation whole broth having an extracellular riboflavin concentration greater than 0.2 g/l.

14. The method of claim 1, wherein said first mixture is fermentation broth comprising lysed cells and riboflavin in a concentration of at least about 0.2 g/l.

15. The method of claim 1, wherein said step of separating said contaminants larger than solubilized riboflavin from said solubilized riboflavin in said second mixture is accomplished by ultrafiltration.

16. The method of claim 15, wherein the pore size used in ultrafiltration is between about $1.0 \times 10^3$ and about $1.0 \times 10^6$ molecular weight cut off.

17. The method of claim 15, wherein the inlet pressure is between about 68 and about 72 psig, and the outlet pressure is between about 16 and about 24 psig.

18. The method of claim 1, wherein said step of separating said remaining contaminants smaller than said riboflavin crystals from said crystallized riboflavin in said fourth mixture is accomplished by ultrafiltration.

19. The method of claim 18, wherein the pore size used in ultrafiltration is between about $1.0 \times 10^4$ molecular weight cut off and about 5 microns.

20. The method of claim 18, wherein the inlet pressure is between about 68 and about 72 psig, and the outlet pressure is between about 16 and about 24 psig.

21. The method of claim 1, wherein said separating step (d) is accomplished by rotary vacuum filtration.

22. The method of claim 1, wherein in step (c) said third mixture is at a temperature between about 75° F. and about 85° F.

23. The method of claim 1, wherein said step of solubilizing is conducted on a first mixture having a temperature of between about 60° F. and about 100° F.

24. The method of claim 1, wherein said step of solubilizing is conducted on a first mixture having a temperature of between about 75° F. and about 85° F.

25. The method of claim 1, wherein said step of separating said contaminants larger than solubilized riboflavin from said solubilized riboflavin in said second mixture is conducted on said second mixture having a temperature of between about 60° F. and about 100° F.

26. The method of claim 1, wherein said step of separating said contaminants larger than solubilized riboflavin from said solubilized riboflavin in said second mixture is conducted on said second mixture having a temperature of between about 75° F. and about 85° F.

27. The method of claim 1, wherein remaining contaminants smaller than said riboflavin crystals from crystallized riboflavin in said third mixture is conducted on a third mixture having a temperature of between about 60° F. and about 140° F.

28. The method of claim 1, wherein said step of separating said remaining contaminants smaller than said crystallized riboflavin from said riboflavin crystals in said fourth mixture is conducted on said fourth mixture having a temperature of between about 70° F. and about 100° F.

29. A method for the recovery of riboflavin from a first aqueous mixture comprising riboflavin and contaminants, said method comprising:
(a) concentrating said first mixture having a temperature of between about 75° F. and about 85° F. to obtain about a 75% reduction in volume of said first mixture, a riboflavin concentration of at least about 20 g/l, or a solids concentration of at least about 180 g/l;
(b) solubilizing the riboflavin in said concentrated first mixture by increasing the pH of said first mixture to between about 12.4 and 12.8 to produce a second mixture having a solubilized riboflavin concentration greater than 0.2 g/l and having a temperature of between about 75° F. and about 85° F.;
(c) separating at least about 75% by weight of contaminants larger than said solubilized riboflavin from said solubilized riboflavin in said second mixture to produce a third mixture comprising solubilized riboflavin and remaining contaminants, said third mixture having a temperature of between about 75° F. and about 85° F.;
(d) precipitating riboflavin from said third mixture by reducing the pH of said third mixture to between about pH 5.8 and about 6.2 and contacting said third mixture with an oxidant to produce a fourth mixture containing riboflavin crystals and remaining contaminants, said fourth mixture having a temperature of between about 70° F. and about 100° F.;
(e) concentrating said riboflavin crystals in said fourth mixture;
(f) separating said riboflavin crystals from said remaining contaminants smaller than said crystallized riboflavin in said concentrated fourth mixture to produce a riboflavin crystal product having a purity of at least 96% by weight; and
(g) drying said riboflavin crystal product.

30. The method of claim 1, wherein said oxidant is an oxygen-containing gas which is contacted with said mixture until the oxygen concentration is from about 50% to about 100% of saturation.

31. The method of claim 1, wherein said oxidant is oxygen in an amount greater than about 5 ppm.

32. The method of claim 1, wherein said step of contacting said mixture with an oxidant comprises aeration.

33. The method of claim 1, wherein said step of contacting said mixture with an oxidant comprises contacting said mixture with an amount of said oxidant that produces an oxidizing environment equivalent to an about 50% to an about 100% oxygen-saturated mixture.

34. The method of claim 1, wherein said riboflavin crystals are separated from said fourth mixture to produce a riboflavin crystal product having a purity of at least 96% by weight.

35. The method of claim 1, wherein at least about 75% by weight of said contaminants that are larger than said solubilized riboflavin are separated from said solubilized riboflavin in Step (b).

* * * * *